United States Patent [19]

McSpadden

[11] Patent Number: 5,067,900

[45] Date of Patent: Nov. 26, 1991

[54] APPARATUS AND METHOD FOR APPLYING GUTTA-PERCHA TO A CARRIER

[76] Inventor: John T. McSpadden, 6918 Shallowford Rd., Chattanooga, Tenn. 37421

[21] Appl. No.: 638,685

[22] Filed: Jan. 8, 1991

[51] Int. Cl.⁵ ............................................. A61G 5/02
[52] U.S. Cl. ...................................... 433/81; 433/224
[58] Field of Search .................. 433/81, 224, 164, 80; 604/200

[56] References Cited

U.S. PATENT DOCUMENTS

| | | | |
|---|---|---|---|
| 2,458,145 | 1/1949 | Coffey | 433/80 |
| 3,850,173 | 11/1974 | Dash | 604/200 |
| 4,353,698 | 10/1982 | McSpadden | 433/81 |
| 4,746,292 | 5/1988 | Johnson | 433/141 |
| 4,758,156 | 7/1988 | Johnson | 433/81 |
| 4,894,011 | 1/1990 | Johnson | 433/81 |

Primary Examiner—John J. Wilson
Attorney, Agent, or Firm—Luedeka, Hodges, Neely & Graham

[57] ABSTRACT

An apparatus and method for applying gutta-percha to a shank-like carrier with which the gutta-percha is introduced into an extirpated root canal utilizes an elongated hollow barrel for holding an amount of gutta-percha and a plunger fitted within the barrel for sliding movement along the length of the barrel. The barrel is provided with a discharge opening at one end thereof into which one end of the shank-like carrier may be inserted. Upon heating the gutta-percha contained within the apparatus to a softened condition, inserting one end of the shank-like carrrier through the discharge opening, and then using the plunger toward the discharge end of the barrel to dispense gutta-percha therefrom while withdrawing the carrier from the discharge opening, the surface of the carrier is coated with the gutta-percha.

15 Claims, 2 Drawing Sheets

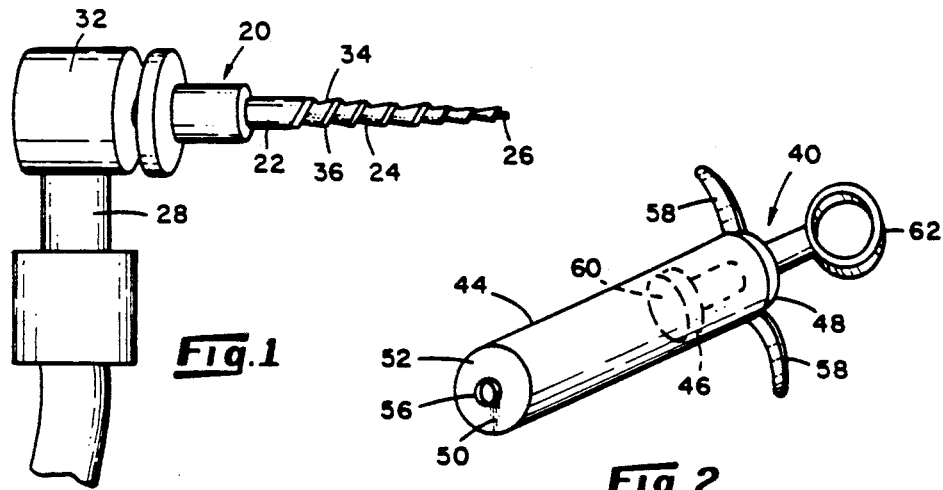
Fig. 1
Fig. 2
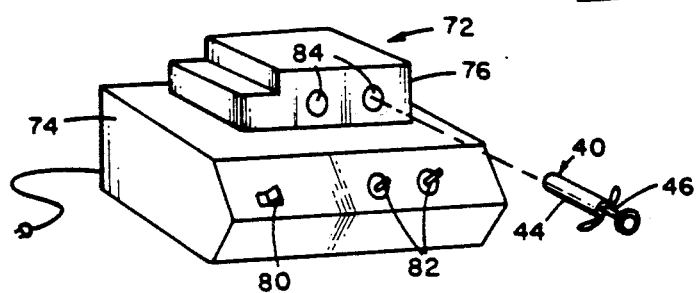
Fig. 3
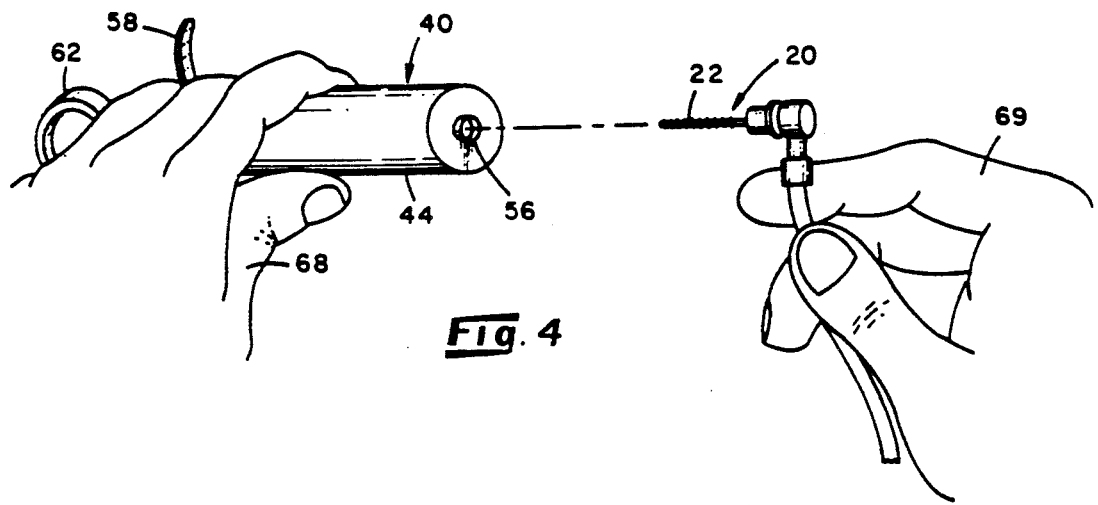
Fig. 4

APPARATUS AND METHOD FOR APPLYING GUTTA-PERCHA TO A CARRIER

The present invention relates generally to the field of endodontics and relates, more particularly, to the obturating of an extirpated root canal.

Known methods of obturating (filling) an extirpated (stripped) root canal commonly involve the packing of a thermoplastic material, such as gutta-percha, into the root canal so that the root canal space is filled with the thermoplastic material. Preferably, the canal space is filled in a homogeneous three-dimensional manner without voids in order to prevent any leakage or communication between the root canal and the surrounding and supporting tissues of the tooth.

It has been found that a satisfactory seal of the root canal space with gutta-percha is obtained upon softening the gutta-percha with heat so that the intricacies and voids of the root canal space are filled with the softened gutta-percha. The most common methods of heating the gutta-percha involve either the application of heat to the gutta-percha while the gutta-percha is positioned inside the root canal or before the gutta-percha is introduced into the root canal. In order to heat gutta-percha when positioned within a root canal, the gutta-percha is manipulated with either a hot probe or a mechanically rotating instrument which heats the gutta-percha with frictional heat generated as the rotating instrument rotates in contact with the gutta-percha. The hot probe or rotating instrument may subsequently be used to manipulate and pack the softened gutta-percha into place.

One method of heating the gutta-percha before its introduction into the canal system involves the heating of gutta-percha contained within a cartridge and then injecting the heated gutta-percha through a needle into the canal. This technique is limited, however, in that the exertion of too much pressure upon the heated gutta-percha through the needle may force the gutta-percha through the foraman of the apex of the root in a manner which could cause medical complications and/or severe pain. Conversely, the exertion of too little pressure upon the gutta-percha through the needle may fail to completely seal the root canal system with the gutta-percha.

Another method of applying heat to gutta-percha prior to its introduction within a root canal involves the placement of gutta-percha on an end of a grooved carrier and then heating the gutta-percha over an open flame. A limitation, however, associated with such a method relates to the difficulty in heating the gutta-percha to the desired temperature without overheating or underheating the gutta-percha. Moreover, heating the gutta-percha over an open flame may not heat the gutta-percha uniformly so that it is softened throughout. In some instances, a carrier is encased with gutta-percha by a manufactured process but such a carrier limits the ability of an endodontist to customize the placement of gutta-percha about the carrier to suit his needs. In particular, the extent to which such a carrier is encased by gutta-percha or the diameter of the gutta-percha encasing such a carrier cannot ordinarily be altered by the endodontist. Still further, carriers which have been encased with gutta-percha by a manufactured process are relatively costly.

It is an object of the present invention to provide an apparatus and method for applying gutta-percha to a carrier instrument for subsequent introduction into an extirpated root canal.

Another object of the present invention is to provide, as an alternative to the aforedescribed prior art methods, a method involving the heating of gutta-percha prior to its introduction into a root canal system.

Yet another object of the present invention is to provide such a method wherein the gutta-percha applied to the carrier instrument is heated uniformly throughout.

Still another object of the present invention is to provide such an apparatus and method which permits an endodontist to customize the encasement of gutta-percha about a carrier instrument to suit his needs.

A further object of the present invention is to provide such an apparatus which is uncomplicated in construction and effective in operation.

More particularly, the invention is embodied in an apparatus and method for applying gutta-percha to a shank-like carrier for subsequent introduction into a root canal system with the carrier. The preferred apparatus includes an elongated hollow barrel for holding an amount of gutta-percha and a plunger fitted within the hollow barrel for sliding movement relative to and along the length of the barrel. The barrel is provided with a discharge opening at one end thereof into which one end of the shank-like carrier may be inserted. When the plunger is moved through the barrel and toward the discharge opening thereof, gutta-percha contained within the barrel is urged toward the discharge opening.

The method of the invention includes the steps of providing the aforedescribed apparatus having an amount of gutta-percha contained within its hollow barrel and heating the apparatus to soften the gutta-percha contained therein. One end of the shank-like carrier is then positioned through the discharge opening of the barrel. The plunger is then urged toward the discharge end of the barrel to dispense the softened gutta-percha through the discharge opening and the carrier is withdrawn from the discharge opening so that gutta-percha dispensed through the discharge opening coats the surface of the carrier.

A more complete understanding of the present invention may be had by reference to the specification and accompanying drawings wherein like numerals refer to like parts throughout.

FIG. 1 is a perspective view of an endodontic instrument having a shank to be coated with gutta-percha in accordance with an embodiment of a method of the present invention.

FIG. 2 is an embodiment of an apparatus with which the method of the invention can be carried out.

FIG. 3 is a perspective view of a heating appliance with which the FIG. 2 apparatus can be heated and illustrating the FIG. 2 apparatus when removed from the heating appliance.

FIGS. 4-6 are views illustrated in sequence various steps involved in the coating of the shank of the FIG. 1 instrument in accordance with an embodiment of a method of the present invention.

Figure 5:
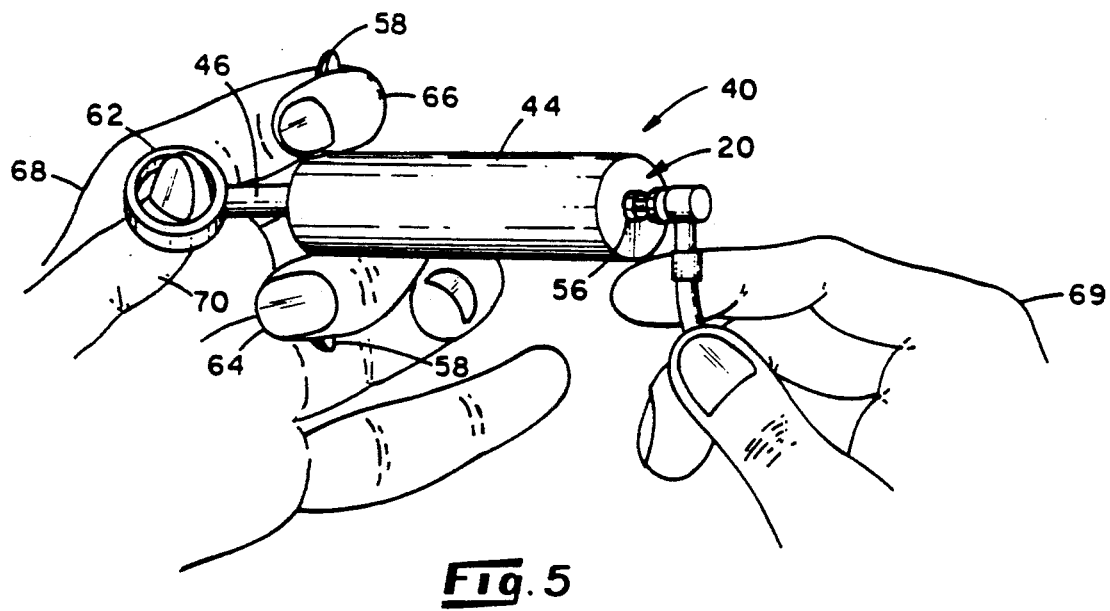

There is illustrated in FIG. 1 an exemplary instrument 20 of a type used to spread and compact filler material, such as gutta-percha, within a root canal space. The instrument 20 includes a rotatable shank 22 having a working portion 24 extending along a substantial portion of the shank length and terminating at a pilot tip 26. During an obturating process in which the gutta-percha is compacted within a root canal space, the instrument shank 22 is inserted within the root canal space and rotated within the root canal at relatively low speeds. To this end, the portion of the shank 22 located above the working portion 24 is provided with a fitting which is adapted to mate with the chuck 32 of a dental handpiece 28 for powering the rotation of the instrument 20 at low speeds or to mate with a handle (not shown) facilitating rotation and manipulation of the instrument 20 by hand.

Although the working portion 2 of the instrument shank 22 may take any of a number of forms, the depicted working portion 24 includes at least one helical flute 34 extending along the length of the working portion 24 so as to provide a downwardly-directed shoulder 36 which spirals along the length of the working portion 24 toward the tip 26 thereof. When the shank 22 is rotated within a root canal in an appropriate direction, filler material which surrounds the shank 22 and also frictionally engages the walls of the root canal is urged by the shoulder 36 downwardly toward and off of the tip 26.

With reference to FIG. 2, there is illustrated an embodiment of an apparatus 40 which can be used to coat the FIG. 1 instrument shank 2 with gutta-percha 42 (FIGS. 6 and 7) in accordance with the method of the present invention. The apparatus 40 resembles a syringe in structure and operation in that it includes an elongated hollow barrel 44 for containing an amount of gutta-percha and a plunger 46 slidably fitted within the barrel 44. As best shown in FIG. 2, the barrel is cylindrical in shape and has two opposite ends 48 and 50. One end 48 of the barrel 44 is open and accepts the plunger 42, and the other end 50 of the barrel 44 is covered by an end wall 52 which is arranged generally perpendicular to the longitudinal axis of the barrel 44. The plunger 46 can be moved along the longitudinal axis of the barrel 44 in either axial direction.

As will be apparent herein, the method of applying a coating of gutta-percha to the FIG. 1 instrument shank 22 involves the insertion of the shank 22 tip-end-first through the barrel end wall 52. Accordingly, the end wall 52 is provided with a central opening 56 sized to loosely accept the instrument shank 22 inserted tip-end-first through the opening 56. In other words, the opening 56 possesses a larger diameter than that of the instrument shank 22 so that when the shank 22 is inserted centrally through the opening 56, an appreciable amount of space exists between the shank 22 and the edge of the opening 56. By way of example, a discharge opening 56 having a diameter within the range of about one to three mm has been found to be suitable size for use with a common instrument shank having a nominal diameter as measured across its shoulder adjacent the tip within the range of about 0.25 mm to 1.40 mm. The barrel 44 also includes a pair of outwardly-extending finger tabs 58 positioned adjacent the barrel end 48 to facilitate the manual urging of the plunger 42 through the barrel 44. If desired, the barrel 44 may be constructed of a transparent material and bear graduations along its cylindrical outer surface.

When using the apparatus 40 to coat an instrument shank in accordance with the present invention, the apparatus 40 has been pre-loaded with an amount of gutta-percha. A process found suitable for filling an apparatus 40 is to remove the plunger 46 from the apparatus barrel 44, heat a large quantity of gutta-percha to a softened state, pour the softened gutta-percha into a large syringe-like tool and then fill the barrel 44 of the apparatus 40 with the large syringe-like tool as the softened gutta-percha is forcibly discharged, or extruded, from the tool into the barrel 44. The plunger 46 is then replaced within the barrel 44, and the gutta-percha contained within the apparatus 40 may be allowed to cool to room temperature.

The plunger 46 of the apparatus 40 is elongated in shape with a head 60 adjacent one end thereof which is slidably received by the barrel 44 and a ring 62 attached to the head 60. The head 60 sealingly engages the inside wall of the barrel 44 so that as the plunger 46 is moved through the barrel 44 in a manner urging gutta-percha toward the end wall 52, gutta-percha is prevented from passing between the head 60 and the inside wall of the barrel 44. In preparation of the apparatus 40 for use, the apparatus 40 is positioned within the palm of the hand 68 as illustrated in FIG. 5 so that the finger tabs 58 are hooked by the middle finger 64 and index finger 66 of the hand 68 and the ring 62 accepts the thumb 70 of the hand 68. The plunger 46 may then be urged into the barrel 44 with the ring 62 as the fingers 64, 66 and thumb 70 are moved toward one another. Because the apparatus 40 is well-suited for use with one hand 68, the other hand of the user is free to hold the FIG. 1 instrument 20 to which gutta-percha is to be applied.

The components 44 and 46 of the apparatus 40 may be constructed of any of a number of suitable materials, such as plastic. It will be understood, however, that in accordance with the method of the invention, the gutta-percha contained within the apparatus is heated in order to soften the gutta-percha. Accordingly, the material of the apparatus components 44 and 46 must be capable of withstanding the temperatures to which the gutta-percha is intended to be raised without experiencing heat-related damage.

The gutta-percha contained within the apparatus 42 for coating the instrument shank 22 preferably possesses a softening temperature of about 140° F. Gutta-percha in its material state is in an "alpha" crystalline form and is known to possess a melting or softening temperature of about 200° F., but may be changed to a "beta" crystalline form having a lower melting temperature, i.e., about 140° F., by heating the gutta-percha to a predetermined temperature and subsequently cooling the gutta-percha at a controlled rate. The process by which the crystalline form of gutta-percha can be changed to thereby lower its melting temperature is known so that a more detailed description of the process is not believed to be necessary. Suffice it to say that by utilizing gutta-percha when in its "beta" crystalline form to coat the instrument shank 22, the gutta-percha is easier to soften, i.e. softens relatively rapidly, and when used at the lower softening temperature of about 140° F., is less likely to harm the tissue of the patient's mouth when placed thereagainst. In addition, the gutta-percha when in its "beta"crystalline form and at about 140° possesses a desirable tackiness for adhering to the instrument shank 22.

With reference to FIG. 3, there is illustrated a heating appliance 72 of a type which is well-suited for heating the apparatus 40 and gutta-percha contained therein to an elevated temperature. The appliance 72 includes a base 74 and a heat-conducting plate 76 mounted upon the base 74. The appliance 72 also includes an electric heating element (not shown) mounted within the base and positioned in heat transfer relationship with the plate 76. When electrical power is delivered to the heating element by way of the cord 78, the plate 76 is heated by the element. Associated with the base 74 is an ON/OFF switch 80 and thermostat control knobs 82 for controlling the temperature to which the plate 76 is raised. The plate 76 includes a pair of openings 84 into which the barrel 44 of the apparatus 40 may be positioned for purposes of heating the apparatus 40. The heating appliance 72 described herein is of known construction and of a type which is well-suited for heating laboratory test tubes positioned within the plate openings 84. Accordingly, a more detailed description of the heating appliance 72 is not believed to be necessary.

In order to apply gutta-percha to the apparatus 72 in accordance with the method of the present invention, the apparatus 72, with gutta-percha contained therein, is heated to an elevated temperature, e.g. about 140° F., in order to soften the gutta-percha. To this end, the apparatus 72 is positioned within one of the openings 84 provided in the plate 76 of the FIG. 3 appliance 72, and the appliance 72 is switched ON to heat the plate 76 and the appliance 72 to an elevated temperature. Preferably, the apparatus 72 is heated and maintained within the plate opening 84 for a lengthy period of time so that the gutta-percha contained within the apparatus 72 is softened throughout.

Figure 6:
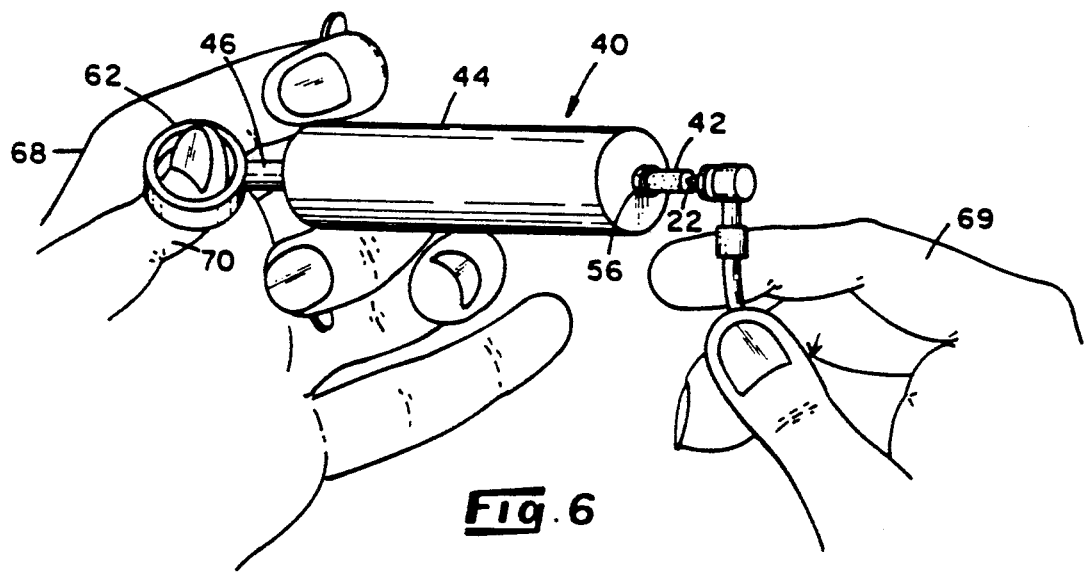

Once the apparatus 40 and the gutta-percha contained therein are raised to the desired elevated temperature, the apparatus 40 is removed from the appliance 72 and the instrument shank 22 (which may be about room temperature) is inserted endwise into the opening 56 provided in the barrel end wall 52 as illustrated in FIG. 4. The shank 22 continues to be inserted into the end wall opening 56 until substantially the entire length of the shank 22 is positioned within the barrel 44 as illustrated in FIG. 5. The middle and index fingers 64, 66 of the hand 68 are then hooked about the apparatus finger tabs 58 and the thumb 70 of the hand 68 as shown in FIG. 5 in preparation for use of the apparatus 40. Pressure is then applied through the ring 62 to the plunger 46 so that the plunger 46 moves toward the barrel end 50 to dispense the softened gutta-percha through the end wall opening 56. As the gutta-percha 42 begins to ooze out of the barrel opening 56, the instrument shank 22 begins to be slowly withdrawn with the other hand, indicated as 69, from the barrel opening 56, as illustrated in FIG. 6. Preferably, the rate at which the shank 22 is withdrawn from the opening 56 is coordinated with the rate at which the plunger 46 is moved toward the barrel end wall 52 so that all of the gutta-percha 42 emitted from the end wall opening 56 adheres to the surface of the instrument shank 22. The enhanced tackiness of the gutta-percha in its "beta" crystalline form and when at about 140° F. is well-suited for sticking the gutta-percha to the shank 22.

It has been found that by withdrawing the instrument shank 22 from the discharge opening 56 at a relatively slow rate applies a relatively thick coating of gutta-percha upon the shank 22. Conversely, while withdrawing the shank 22 from the opening 56 at a faster rate applies a thinner coating of gutta-percha upon the shank 22. Therefore, by coordinating the rate at which the plunger 46 is urged toward the barrel end wall 52 with the rate at which the shank 22 is withdrawn from the barrel opening 56, a user may control the thickness of the gutta-percha coating applied to the shank 22. Accordingly, the method of the present invention enables an endodontist to control the extent to which the shank 22 is coated with gutta-percha and the thickness of the gutta-percha coating applied about the shank 22.

Figure 7:
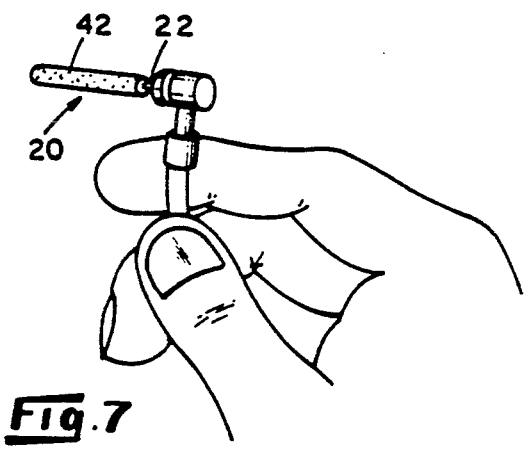
FIG. 7 is a perspective view of the FIG. 1 instrument having a shank which has been coated in accordance with the method of the present invention.

With the softened gutta-percha applied about the shank 22, as illustrated in FIG. 7, the shank 22 is inserted into an extirpated root canal space for introducing the gutta-percha into the space. By rotating and appropriately manipulating the shank 22 in a conventional manner, the gutta-percha is transferred from the shank 22 to the walls of the root canal where it is compacted within the canal space.

It will be understood that numerous modifications and substitutions can be had to the aforedescribed embodiments without departing from the spirit of the invention. Accordingly, the aforedescribed embodiments are intended for the purpose of illustration and not as limitation.

I claim:

1. A method of applying gutta-percha to a shank-like carrier with which the gutta-percha is introduced into an extirpated root canal for obturating the root canal, said method comprising the steps of:
   providing a syringe-like apparatus having a hollow barrel containing an amount of gutta-percha and a plunger fitted within the barrel for sliding movement relative to and along the length of the barrel, one end of the barrel having a discharge opening toward which the gutta-percha is urged when the plunger is moved through the barrel and toward the discharge opening;
   heating the apparatus to soften the gutta-percha contained therein;
   positioning one end of the shank-like carrier through the discharge opening; and
   moving the plunger through the barrel to dispense the softened gutta-percha through the discharge opening and withdrawing the carrier from the discharge opening so that gutta-percha dispensed through the discharge opening coats the surface of the carrier.

2. The method of claim 1 wherein the step of heating is carried out over a period of time to raise the entire amount of gutta-percha contained within the apparatus to a softening temperature.

3. The method of claim 1 wherein the step of positioning includes a step of inserting the one end of the carrier through the discharge opening so that a substantial portion of the length of the carrier is positioned within the barrel of the apparatus.

4. The method of claim 1 wherein the steps of moving and withdrawing are performed substantially simultaneously.

5. The method of claim 1 wherein the steps of moving and withdrawing are coordinated so that the gutta-percha dispensed from the apparatus evenly coats the carrier along its length.

6. The method of claim 1 wherein the step of withdrawing includes a step of maintaining the carrier substantially centrally of the discharge opening as the carrier is withdrawn from the discharge opening so that the carrier is substantially centered within the gutta-percha dispensed through the discharge opening.

7. A method of coating a shank-like carrier with gutta-percha for introduction of the gutta-percha into an extirpated root canal, said method comprising the steps of
   providing a syringe-like apparatus having a hollow barrel containing an amount of gutta-percha and a plunger fitted within the barrel for sliding movement relative to and along the length of the barrel, the barrel being provided with a discharge opening at one end thereof through which the gutta-percha is dispensed when the plunger is moved through the barrel and toward the discharge opening;

heating the apparatus to an elevated temperature to soften the gutta-percha contained therein;

inserting one end of the carrier through the discharge opening until a substantial portion of the length of the carrier is positioned within the barrel; and moving the plunger toward the discharge end of the barrel to dispense the softened gutta-percha through the discharge opening and withdrawing the carrier from the discharge opening so that the gutta-percha dispensed through the discharge opening coats the surface of the carrier.

8. The method of claim 7 wherein the step of heating is carried out over a period of time to raise the entire amount of gutta-percha contained within the apparatus to a softening temperature.

9. The method of claim 7 wherein the steps of moving and withdrawing are performed substantially simultaneously.

10. The method of claim 7 wherein the steps of moving and withdrawing are coordinated so that the gutta-percha dispensed from the apparatus evenly coats the carrier along its length.

11. The method of claim 7 wherein the step of withdrawing includes a step of maintaining the carrier substantially centrally of the discharge opening as the carrier is withdrawn from the discharge opening so that the carrier is substantially centered within the gutta-percha dispensed through the discharge opening.

12. In an applicator for applying a coating of gutta-percha to the shank of a shanked carrier for subsequent introduction of the gutta-percha into a root canal with the carrier, the combination comprising:

an amount of gutta-percha;

an apparatus including an elongated hollow barrel within which the amount of gutta-percha is positioned, the barrel having a discharge opening at one end thereof into which one end of the shank of a shanked carrier may be inserted for exposure to the gutta-percha contained therein, the barrel being sized to be positioned between two fingers of a user's hand for use of the apparatus;

a plunger fitted within the hollow barrel for sliding movement relative to and along the length of the barrel;

means associated with the plunger and barrel permitting the barrel to be braced against movement when held between two fingers of one of the user's hands and permitting the plunger to be moved by the thumb of the user's one hand relative to and along the length of the barrel;

said amount of gutta-percha having been processed to render the gutta-percha extrudable through the discharge opening of the barrel when heated to a softening temperature so that upon heating the apparatus to soften the gutta-percha contained therein, subsequently holding the apparatus with one hand so that the barrel is braced against movement between the two fingers of the one hand and the plunger can be moved with the thumb of the one hand as aforesaid, and inserting one end of the carrier shank through the discharge opening and moving the plunger toward the discharge end of the barrel to dispense gutta-percha therefrom while withdrawing the carrier from the discharge opening, the surface of the carrier is coated with the gutta-percha.

13. The combination of claim 12 wherein the discharge opening of the barrel is sized to loosely receive the shank of the carrier when inserted endwise therein.

14. The combination of claim 12 wherein the diameter of the discharge opening of the barrel is within the range of about one to three millimeters.

15. The combination of claim 12 wherein the associated means includes finger tabs joined to the barrel facilitating the bracing of the barrel against movement when positioned between the two fingers of the user's one hand.

* * * * *